United States Patent [19]

Vogelbach

[11] Patent Number: 4,844,058

[45] Date of Patent: Jul. 4, 1989

[54] BIOMECHANICAL ANKLE BRACE

[76] Inventor: W. Daniel Vogelbach, 1000 J. D. Anderson Dr., Morgantown, W. Va. 26505

[21] Appl. No.: 145,713

[22] Filed: Jan. 15, 1988

[51] Int. Cl.⁴ ............................................. A61F 13/06
[52] U.S. Cl. .................................. 128/80 R; 128/80 H
[58] Field of Search ...................... 128/80 R, 153, 166, 128/171, 80 H, 80 A, 165, 155

[56] References Cited

U.S. PATENT DOCUMENTS

| | | | |
|---|---|---|---|
| 1,564,874 | 12/1925 | Madden | 128/165 |
| 1,624,266 | 4/1927 | Luder | 128/166 |
| 3,050,053 | 8/1962 | Peckham | 128/166 |
| 3,073,305 | 1/1963 | Biggs, Jr. et al. | 128/166 |
| 3,357,425 | 12/1967 | Morgan | 128/166 |
| 3,490,450 | 1/1970 | Gardner | 128/171 |
| 3,506,000 | 4/1970 | Baker | 128/80 R |
| 3,508,544 | 4/1970 | Moore et al. | 128/153 |
| 3,674,023 | 7/1972 | Mann | 128/166 |
| 4,141,358 | 2/1979 | DeMarco | 128/166 |
| 4,197,845 | 4/1980 | Browning | 128/153 |
| 4,289,122 | 9/1981 | Mason et al. | 128/80 H X |
| 4,554,912 | 11/1985 | Haberman | 128/80 E |
| 4,729,370 | 3/1988 | Kallasy | 128/80 H |
| 4,753,229 | 6/1988 | Sutherland | 128/80 H |

Primary Examiner—Robert A. Hafer
Assistant Examiner—Jeffrey L. Thompson
Attorney, Agent, or Firm—Berman, Aisenberg & Platt

[57] ABSTRACT

A brace for treating an ankle comprises an elastic sleeve having a plurality of elastic straps secured to the sleeve. The sleeve is attached to the patient's ankle, and the elastic straps are wrapped around the ankle. The straps are designed to extend parallel to and support particular ligaments and/or muscles to provide efficient treatment of the ankle. In accordance with a method, the ankle is cast in plaster of paris and the elastic straps are accurately located with respect to the relevant ligaments and tendons of the patient.

7 Claims, 2 Drawing Sheets

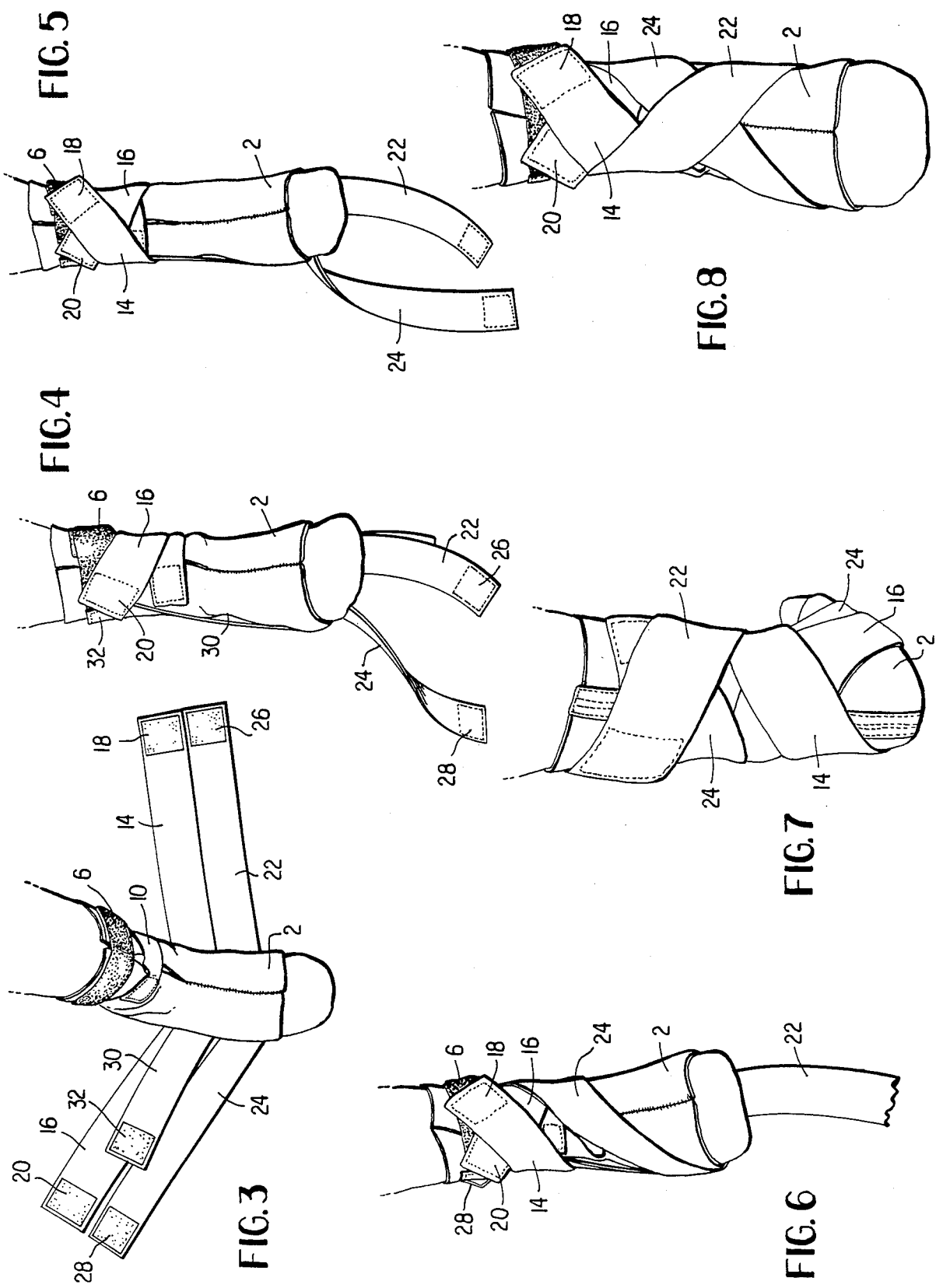

BIOMECHANICAL ANKLE BRACE

TECHNICAL FIELD

This invention relates to the art of orthopedic braces. In particular, the invention relates to a brace for use in treatment of injuries relating to the foot and ankle.

BACKGROUND ART

In the treatment of ankle injuries, such as sprains, it is known to wrap the ankle to stabilize it. For example, the ankle can be wrapped with adhesive tape or with an elastic bandage to immobilize the ankle to allow it to heal.

Other devices have been developed for treatment of ankle injuries which employ a sock-like element having elastic straps attached thereto for being wrapped around the ankle. U.S. Pat. No. 4,313,433 (Cramer) shows a device for attachment to an ankle wherein a flexible jacket is secured to the ankle by a shoelace. The jacket has two straps attached to its bottom, and these straps are wrapped around the ankle and secured to themselves. U.S. Pat. No. 4,141,358 (DeMarco) teaches a device having an inner sock-like part and outer straps for wrapping about the ankle. U.S. Pat. No. 4,597,395 (Barlow et al.) teaches an ankle support device wherein an ankle-engaging portion has two straps, one of which engages the ankle, and the second of which engages the plantar portion of the foot and extends over the top of the foot. U.S. Pat. No. 3,490,450 (Gardner) teaches an ankle jacket which is secured to the foot and includes an elongate strap for being wrapped around the ankle. U.S. Pat. No. 3,506,000 (Baker) shows an ankle support wherein a first portion is secured to the rear of the ankle adjacent the achilles tendon and includes an elongate strap for wrapping about the ankle and foot. U.S. Pat. No. 4,367,733 (Stromgren) teaches an ankle support comprising a sock-like elastic sheath having an elongate elastic panel for wrapping around the foot of the patient.

Prior art braces, such as those described above, do not adequately account for the various motions of the ankle and have not been successful. The joints in the foot and ankle move in a tri-planer motion, the axis of motion being different for each articulation and the midtarsal joint having two axes of motion. When ankle sprains occur, the ligaments and surrounding structures of the talocrural joint as well as those of the midtarsal and subtalar joints are sprained or strained. Prior techniques have failed to control articulations associated with these joints. Moreover, ankle sprains occur by several different mechanisms including inversion, eversion, supination-adduction, pronation-external rotation, and pronation-abduction. External support mechanisms have failed to provide the required stabilization for the joints of the foot and ankle to help prevent all ankle sprains.

SUMMARY OF THE INVENTION

The inventive brace has been designed to control the foot and ankle both as a functional unit and as individual articulations. The brace may be custom fitted, or it may be sold over the counter in various sizes.

The new brace provides more stability because stabilizing straps can be placed in biomechanically correct positions for the foot and ankle, thus optimizing efficiency.

In a preferred embodiment, the brace of the invention comprises an elastic sleeve made of Neoprene that fits over the ankle, a portion of the foot, and a portion of the leg. The sleeve includes bands by which it can be securely fitted to the patient's foot and ankle. Five elastic straps are sewn to the bottom (plantar) portion of the sleeve for being wrapped around the sleeve to secure the ankle.

The elastic straps parallel selected muscles and/or ligaments in the foot to support them. Preferably, a mold is made of the patient's foot by casting it in plaster of paris whereby the sleeve can be made to be the exact size of the patient's foot and the elastic straps can be more accurately positioned.

A first strap is placed on the plantar surface of the sleeve and extends upwardly and rearwardly to attach to a Velcro (or the like) strip at the upper edge of the sleeve.

Two straps are placed on the plantar portion of the sleeve toward the rear of the sleeve and extend onto opposite sides of the sleeve. A first of these straps extends around the back of the ankle and spirals upwardly around the lower leg to be attached to the upper front of the sleeve. The second of these straps spirals around the other side of the ankle and attaches to the upper front part of the sleeve also.

A second set of straps is attached to the plantar surface of the sleeve in the forefoot region. A first of these straps extends upwardly and crosses over the base of the fifth metatarsal head and spirals upwardly to attach to an upper rear portion of the sleeve. The second of these two straps is also attached to the plantar surface of the sleeve and extends upwardly to traverse the anterior aspect of the ankle and cross the first strap.

It is an object of this invention to provide a brace for an ankle wherein a plurality of elastic straps provides unique support for the ligaments and muscles.

Another object of this invention is to provide a brace for an ankle wherein elastic straps follow selected muscles and/or tendons to provide support.

Yet another object of this invention is to provide a method for supporting an ankle wherein an ankle is cast and a sleeve with accurately positioned elastic elements is attached to the ankle.

BRIEF DESCRIPTION OF THE DRAWINGS

FIGS. 3 through 8 illustrate progressive steps in applying the brace of the invention.

DETAILED DESCRIPTION OF THE PREFERRED EMBODIMENT

Figure 1:
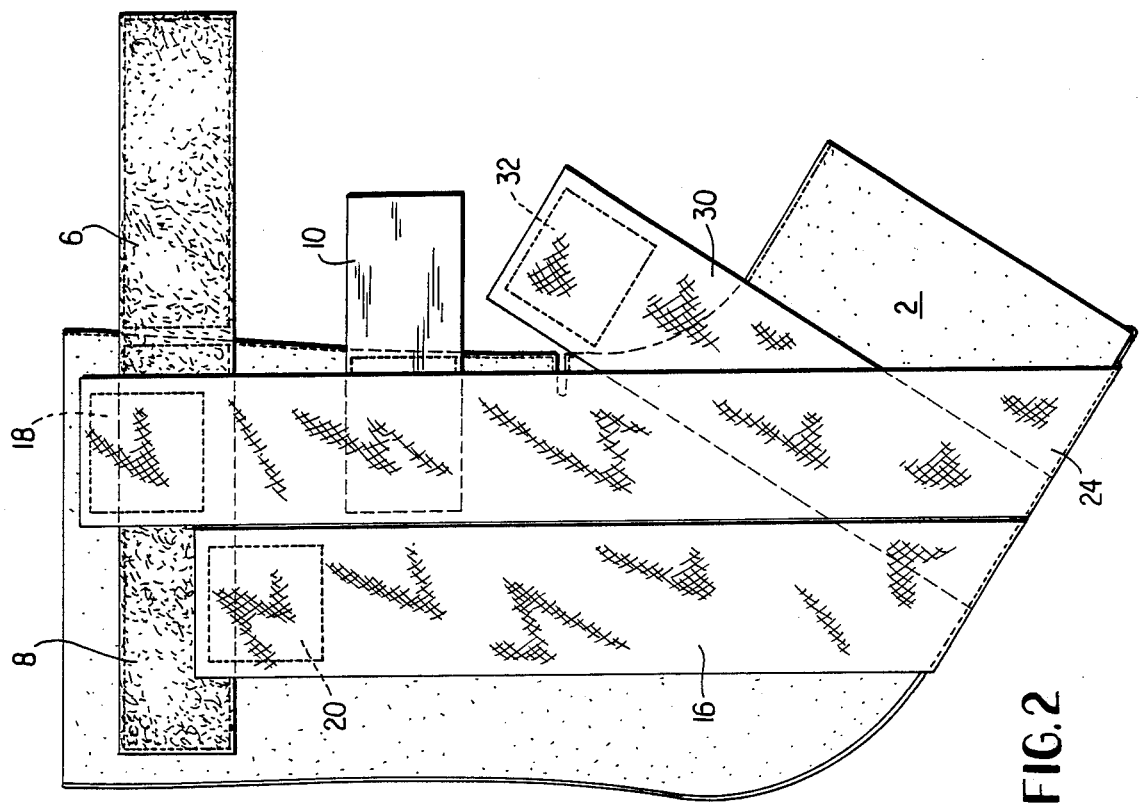
FIG. 1 is a left side view of a sleeve in accordance with the invention.
Figure 2:
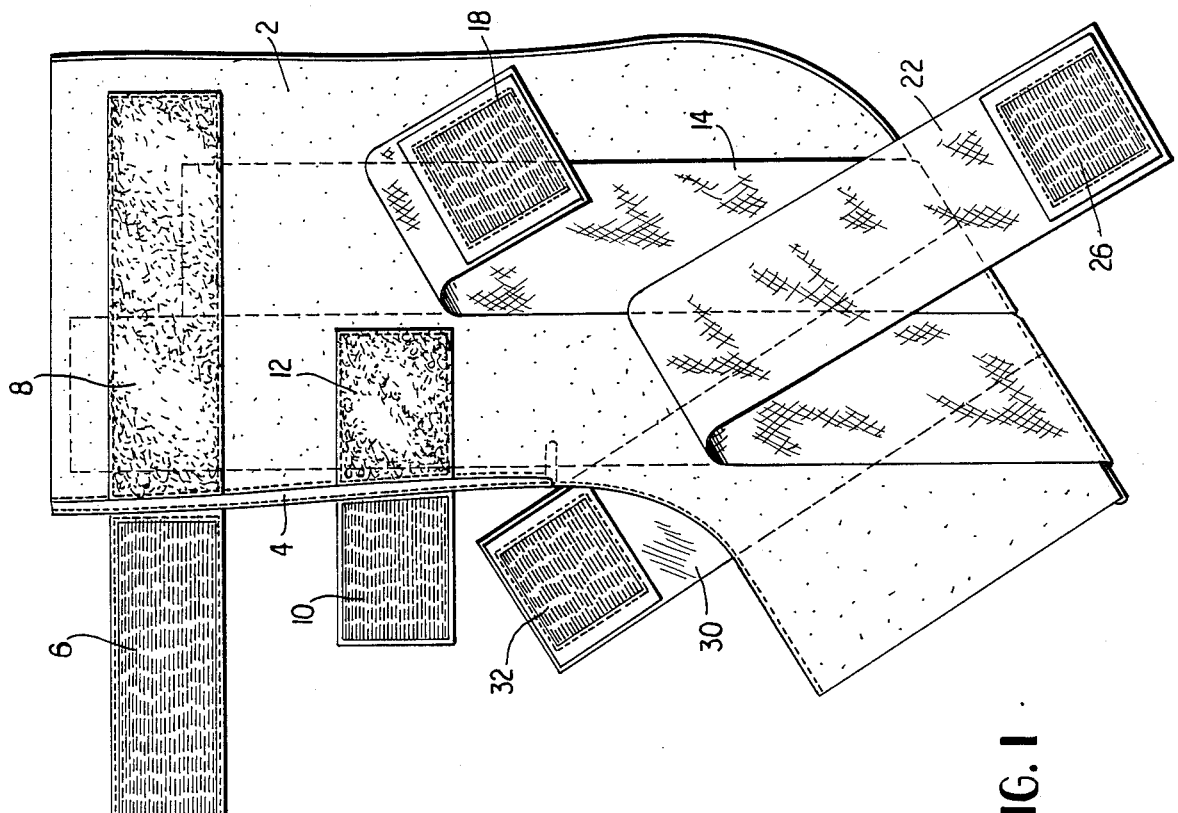
FIG. 2 is a right side view of a sleeve in accordance with the invention.

FIG. 1 is a left side view of an elastic sleeve 2 for being fitted over a right foot and ankle of a patient. The sleeve extends from the base of the calf to just above the toes and includes a slit 4 for permitting the patient's foot to be inserted. A band 6 is attached at an upper end of the sleeve 2 for cooperation with a strip 8 to secure the upper portion of the sleeve to the patient's leg. A second band 10 cooperates with a strip 12 also to secure the sleeve to the patient's leg and foot. Preferably, bands 6 and 10 and strips 8 and 12 are cooperating portions of a hook and loop material such as Velcro. Strip 8 extends substantially around the top of sleeve 2 except for a gap in the rear to permit the elasticity of the sleeve 2 to assist in securing the sleeve to the leg. Preferably, strip 8 is arranged at a slight spiral with respect to a central axis of the sleeve so that tightening of band 6 and strip 8 does not cut off flow of blood to the patient's foot.

Strip 8 is longer than strip 6 and provides additional loop material for cooperation with hook material on elastic straps in a manner to be described below. In addition, the outer surface of band 6 includes a loop material for cooperation with hook material on the elastic straps.

A first set of straps 14 and 16 is attached to a rearward portion of the bottom of elastic sleeve 2. Strap 14 includes a hook material 18 at an upper edge thereof for attachment to the loop material of strip 8 or the loop material on the outer surface of band 6. Similarly, elastic strap 16 includes a hook material 20 also for attachment to hook material on strip 8 or band 6. A second set of elastic straps 22 and 24 are attached to a forward portion of the bottom of the elastic sleeve 2, and each has a hook material 26 and 28, respectively for cooperation with strip 8 or the outer surface of band 6. A fifth elastic strap 30 is attached to the outer bottom portion of elastic sleeve 2 and includes a hook material 32 for attachment to strip 8 or the outer surface of band 6.

It will appreciated that hook and loop material such as Velcro is preferred but that any of a wide variety of attachment devices may be employed.

With reference to FIGS. 3 through 8, the functions of the above-described elements will be set forth in more detail.

With reference to FIG. 3, elastic sleeve 2 has been fitted onto a foot and leg of a patient, and bands 6 and 10 have been applied to secure the elastic band to the patient. In FIG. 4, elastic strap 30 has been pulled upwardly and slightly rearwardly to be attached to a side portion of strip 8. This strap resists calcaneal inversion and distraction forces on the lateral collateral ligaments of the ankle joint.

FIG. 4 also illustrates how strap 16 has been wrapped around the rear of the ankle and secured to the top of sleeve 2 at band 6. FIG. 5 illustrates how strap 14 has been wrapped in a manner similar to that of strap 16 but in an opposite direction. Straps 14 and 16 extend around the ankle joint and spiral upwardly. Strap 16 resists inversion of the calcaneus and supination of the subtalar joint. It increases the lever arm of the extensor digitorium longus as a subtalar joint pronator and as a talocrural joint dorsiflexor. In addition, strap 16 increases the lever arm of the peroneus longus and brevis muscles at the subtalar joint thus increasing the pronation forces. It parallels and supports the anterior talofibular ligament and the posterior band of the interosseus talocrural ligament.

Strap 14 is the partner of strap 16. It is positioned to resist eversion and anteromedial forces (subtalar pronation). Biomechanically, this strap increases the lever arm of the posterior tibialis tendon at the subtalar joint which decelerates pronation and internal rotation of the foot and supinates the subtalar joint. It also increases the lever arm of the posterior tibialis tendon on the talocrural joint which helps the soleus and long digita flexors decelerate anterior movement of the tibia with forefoot contact. Flexor digitorum longus lever arm is increased at the talocrural joint to aid in plantar flexion and at the subtalar joint to aid in supination. Strap 14 also parallels and helps support the anterior talotibial ligament.

FIG. 6 illustrates how strap 24 is applied over the top part of the foot and around the rear of the upper part of the elastic sleeve 2. Strap 24 extends from the plantar surface of the sleeve in the forefoot region to run laterally and cross over the base of the fifth metatarsal head. It spirals upwardly to support the calcaneocuboid joint and crosses the anterior aspect of the talocrural joint. The primary function of this strap is to resist subtalar and talocrural joint inversion. Strap 24 cooperates with strap 22 to resist anterior gliding of the talus where the talocrural joint is in an open packed position and is thus unstable.

Strap 22 is applied in a manner similar to that of strap 24 in that it extends across the top of the foot and spirals around to be attached to a rear part of band 6. Strap 22 supports the medial longitudinal arch and resists abnormal anterior translation of the talus. Biomechanically, it increases the lever arm of the tibialis anterior tendon to resist pronation of the forefoot around the longitudinal axis of the midtarsal and pronation of the subtalar joint. Strap 22 also increases the lever arm of the posterior tibialis tendon to the oblique axis of the midtarsal joint to supinate the forefoot or resist pronation.

FIG. 7 is a rear view of a patient's ankle having the brace of the invention secured thereto. FIG. 8 is a front view of the brace when fully installed.

In a preferred method for treating a patient, the patient's foot and ankle are cast in plaster of paris, the particular bones and tendons noted above being marked with ink such that the plaster cast carries an indication of the relevant bones and ligaments. Then, the sleeve 2 and elastic straps 14, 16, 22, 24, and 30 are located on the elastic sleeve to correspond accurately with the muscles and tendons being treated.

It will be appreciated that a unique brace and method for construction of the brace have been described. Modifications within the scope of the appended claims will be apparent to those of skill in the art.

I claim:

1. Apparatus for controlling a forefoot, rearfoot and ankle comprising a sleeve for fitting over a foot and ankle, and at least five elastic straps attached to the bottom of the portion of said sleeve which fits over said foot, wherein said elastic straps comprise a first strap extending to an outer side of said sleeve, second and third straps extending to opposite sides of said sleeve and fourth and fifth straps extending to opposite sides of said sleeve and attached to said sleeve forward of said second and third straps, and securing means attached to an upper portion of said sleeve for securing the ends of said straps to said sleeve, and wherein said first strap is adapted to extend from said bottom of said sleeve to said securing means without wrapping around said foot, said second and third straps are adapted to extend from said bottom of said sleeve, around the back of the foot and then to said securing means, and said fourth and fifth straps are adapted to extend from said bottom of said sleeve across the top of the foot, around the back of the foot and to said securing means.

2. Apparatus according to claim 1 wherein said securing means comprises a band for holding the upper portion of said sleeve to a leg.

3. Apparatus according to claim 1 wherein said first strap extends along the outside of said ankle to a position on said securing means rearward of the connection between said sleeve and said first step strap.

4. Apparatus according to claim 3 wherein said second and third straps attach to a front portion of said securing means and said fourth and fifth straps attach to a rear portion of said securing means.

5. A method for controlling a forefoot, rearfoot and ankle comprising attaching a sleeve over a foot and ankle, said sleeve comprising at least five elastic straps attached to the bottom of the portion of said sleeve which fits over said foot, said elastic straps comprising a first strap extending to an outer side of said sleeve, second and third straps extending to opposite sides of said sleeve and fourth and fifth straps extending to opposite sides of said sleeve and attached to said sleeve forward of said second and third straps, and securing means being attached to an upper portion of said sleeve for securing the ends of said straps to said sleeve, attaching said first strap to said securing means without wrapping around said foot, wrapping said second and third straps from said bottom of said sleeve, around the back of the foot and then to said securing means, and wrapping said fourth and fifth straps from said bottom of said sleeve across the top of the foot, around the back of the foot and to said securing means.

6. A method according to claim 5 wherein said step of attaching said first strap comprises extending said first strap along the outside of said ankle to a position on said securing means rearward of the connection between said sleeve and said first strap.

7. A method according to claim 6 wherein said second and third straps are attached to a front portion of said securing means and said fourth and fifth straps are attached to a rear portion of said securing means.

\* \* \* \* \*